United States Patent
Buschle et al.

(10) Patent No.: US 12,266,126 B2
(45) Date of Patent: Apr. 1, 2025

(54) MEASURING METHOD AND A MEASURING DEVICE FOR MEASURING AND DETERMINING THE SIZE AND DIMENSION OF STRUCTURES IN SCENE

(71) Applicant: KARL STORZ SE & Co. KG, Tuttlingen (DE)

(72) Inventors: Lukas Buschle, Tuttlingen (DE); Simon Haag, Tuttlingen (DE); Jasmin Keuser, Tuttlingen (DE); Benedikt Köhler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 198 days.

(21) Appl. No.: 17/870,463

(22) Filed: Jul. 21, 2022

(65) Prior Publication Data
US 2023/0032791 A1    Feb. 2, 2023

(30) Foreign Application Priority Data
Jul. 27, 2021 (DE) ................. 10 2021 119 481.4

(51) Int. Cl.
*G06T 7/571* (2017.01)
*A61B 1/00* (2006.01)
(Continued)

(52) U.S. Cl.
CPC .......... *G06T 7/571* (2017.01); *A61B 1/00009* (2013.01); *A61B 1/0669* (2013.01); *G06T 7/593* (2017.01); *G06T 2207/10068* (2013.01)

(58) Field of Classification Search
CPC ................ G06T 7/571; G06T 7/593; G06T 2207/10068; G06T 7/55; G06T 7/50;
(Continued)

(56) References Cited

U.S. PATENT DOCUMENTS

| 4,895,431 A | 1/1990 | Tsjiuchi et al. |
| 6,094,215 A | 7/2000 | Sundahl et al. |
(Continued)

FOREIGN PATENT DOCUMENTS

| DE | 102011114146 A1 | 3/2013 |
| DE | 10100335 B4 | 2/2017 |
(Continued)

OTHER PUBLICATIONS

Bengisu Ozyoruk, Kutsev et al. "EndoSLAM Dataset and an Unsupervised Monocular Visual Odometry and Depth Estimation Approach for Endoscopic Videos: Endo-SfmLearner" Medical Image Analysis; Oct. 2, 2020.
(Continued)

*Primary Examiner* — Brandon J Miller
(74) *Attorney, Agent, or Firm* — Jason H. Vick; Amped IP LLC

(57) ABSTRACT

An exemplary embodiment relates to a measuring method (50) and to a measuring device (10) in order to determine a length or an area within a scene (32) which are characterized at least partially by a real start point (40-2) and a real end point (42-2), wherein the measurement takes place using at least two images (18, 20) and it is thereby not necessary for the real start point (40-2) and the real end point (42-2) to be imaged in one of the images (18, 20).

15 Claims, 8 Drawing Sheets

(51) Int. Cl.
*A61B 1/06* (2006.01)
*G06T 7/593* (2017.01)

(58) Field of Classification Search
CPC . A61B 1/00009; A61B 1/0669; A61B 5/1079; A61B 2090/061; A61B 2090/364; A61B 1/0605; A61B 1/00057; A61B 5/1076; A61B 1/000094; G16H 20/40; G16H 50/50; G16H 30/20
See application file for complete search history.

(56) References Cited

U.S. PATENT DOCUMENTS

| | | | |
|---|---|---|---|
| 6,741,948 | B2 | 5/2004 | Hauger et al. |
| 8,870,750 | B2 * | 10/2014 | Fehre ................... A61B 90/36 600/117 |
| 10,441,146 | B2 | 10/2019 | Inoue |
| 2007/0161854 | A1 | 7/2007 | Alamaro et al. |
| 2016/0302653 | A1 | 10/2016 | Inoue |
| 2019/0096135 | A1 | 3/2019 | Dal Mutto et al. |
| 2019/0142250 | A1 | 5/2019 | Maas et al. |
| 2020/0279386 | A1 | 9/2020 | da Veiga |
| 2020/0345291 | A1 * | 11/2020 | Bradley ................... A61B 1/05 |
| 2020/0387706 | A1 | 12/2020 | Zur |
| 2021/0082568 | A1 * | 3/2021 | Kamon ................. G16H 30/40 |
| 2021/0152802 | A1 | 5/2021 | Varekamp et al. |
| 2022/0375114 | A1 * | 11/2022 | Hunter ............. A61B 1/000094 |

FOREIGN PATENT DOCUMENTS

| | | |
|---|---|---|
| EP | 1965699 B1 | 6/2017 |
| EP | 3484338 B1 | 2/2024 |
| JP | 5777317 B2 | 9/2015 |
| WO | WO 2019/213432 A1 | 11/2017 |
| WO | WO 2021/138262 A1 | 7/2021 |

OTHER PUBLICATIONS

Blank, Christian "Generierung von Tiefenbildern mittels Stereoskopie" Hochschule für Angewandte Wissenschaften Hamburg; Hamburg University of Applied Sciences; Sep. 13, 2013.

Bodenstedt, Sebastian et al. "Image-Based Laparoscopic Bowel Measurement" International Journal of Computer Assisted Radiology and Surgery; Sep. 26, 2015.

Hirschmüller, Heiko "Accurate and Efficient Stereo Processing by Semi-Global Matching and Mutual Information" IEEE Conference on Computer Vision and Pattern Recognition (CPVR), Jun. 20-26, 2005.

Hirschmüller, Heiko "Semi-Global Matching—Motivation, Developments and Applications" Photogrammetric Week, Sep. 2011.

Hottong, Nikolaus "Stereoskope HD Produktionen—Messungen statt Mythen" Publication series Digital Media Faculty of HFU Furtwangen University, Dec. 2016, ISBN 3-9810384-9-5.

Thormahlen, Thorsten et al. "Three-Dimensional Endoscopy" 2003.

Office Action for Corresponding German Patent Application No. 10 2021 119 481.4, mailed Jul. 27, 2021.

European Search Report for corresponding European Patent Application No. 22185947.3, mailed Dec. 16, 2022.

* cited by examiner

MEASURING METHOD AND A MEASURING DEVICE FOR MEASURING AND DETERMINING THE SIZE AND DIMENSION OF STRUCTURES IN SCENE

CROSS-REFERENCE TO RELATED APPLICATIONS

This application claims the benefit under 35 U.S.C. 119(a) to German Patent Application No. 10 2021 119 481.4, filed 27 Jul. 2021, the disclosure of which is incorporated herein by reference in its entirety.

BACKGROUND

An exemplary embodiment relates to a measuring method and to a measuring device.

Optical visualization systems, such as microscopes, exoscopes and endoscopes make it possible to represent a scene. The scene is usually a work region in which work requiring fine-motor skills or visual checks are carried out. In the case of medical interventions, the work region is an operating field in an inner region of the human body.

Endoscopy is for example an imaging technique in which an endoscope is introduced into a cavity. The specialist personnel, who carry out such an intervention using an endoscope, view the image captured by the endoscope on the screen and can direct their actions accordingly. In the case of medical interventions, an endoscope is introduced into the body in order to capture an inner image of the body and display it on the screen. Such interventions using endoscopy, which are also referred to in medicine as minimally-invasive surgery, generally only require significantly smaller incisions than conventional methods, such as e.g. open surgery since it is not necessary to have a direct view of a region, at which the intervention is carried out.

Due to the required precise way of working of the specialist personnel, it is desirable that an exact image of the cavity or region is provided, at which the inspection or operation is performed. Generally, images represented by an endoscope on a display device are two-dimensional and it is therefore not possible for the specialist personnel to easily or reliably determine the dimensions and measurements of structures in the imaged scene. This represents a challenge for the required precise way of working.

The two-dimensional and often magnified representation of structures in a scene, which can also be distorted in the case of wide-angle recordings without rectification, in fact frequently leads to the dimensions and measurements of the structure in the scene being perceived incorrectly. In many cases, it is therefore desirable for the specialist personnel to have a simple measuring function. In the case of medical interventions, this can for example serve to measure the size of a craniotomy, an aneurysm, tumors or any other desired anatomical structure in an intraoperative manner.

In the case of medical interventions, the estimation of a distance, which is associated with the inner anatomy of a patient during a minimally-invasive surgical intervention, can include positioning robotically-operated surgical instruments to different positions within the patient and estimating the distance between the instruments based on kinematic data for the instruments.

It is also possible to determine via the focus position of the medical instrument, such as e.g. of the endoscope, a working distance from the anatomical structure, in order to calculate and display real distances in the recorded image using this information. This can for example take place in the form of a scale.

DE 10 2011 114 146 A1 discloses for example a method and a device for representing an object, which makes it possible to assess the dimension of the object as effectively as possible. The object is for example tissue and the disclosed method can be used to control an operation on the tissue.

In spite of some promising approaches, there is still the need for it to not only be possible to reliably measure and determine the size of structures in the recorded scene when a static image of the scene has been recorded, but also for this to be possible, for example even at the same time as the movement of the instrument during the inspection or intervention. In this case, it would make it possible for the specialist personnel to, among other things, determine the size of a structure in real time during the inspection or intervention. The specialist personnel could then better direct their actions based on this and draw conclusions that were previously not possible.

In light of this, one aspect of the disclosed technology provides a simple and improved measuring method as well as a corresponding measuring device, by means of which the specialist personnel can determine the size and dimension of structures in a scene.

According to one aspect, one object is achieved by a measuring method, having the following steps:

Recording a first image of a scene, wherein recording takes place using an image sensor, in front of which an optical system is arranged, wherein, in the first image, a first plurality of first image points image a corresponding first plurality of first real points of the scene by means of the image sensor and wherein an image start point of the first plurality of first image points defines a real start point in the scene, wherein, when the first image is recorded, a viewing field of the image sensor is located in a first spatial position relative to the scene;

Identifying first depth information which describes, at least for a first subset of the first plurality of first image points, including the image start point, a respective distance of a first real point of the first plurality of first real points imaged by a first image point from a reference plane;

Recording a second image of the scene, wherein recording takes place using the image sensor, wherein, in the second image, a second plurality of second image points image a corresponding second plurality of second real points of the scene by means of the image sensor and wherein an image end point of the second plurality of second image points defines a real end point in the scene, wherein, when the second image is recorded, the viewing field of the image sensor is located in a second spatial position relative to the scene, which differs from the first spatial position;

Identifying second depth information which describes, at least for a second subset of the second plurality of second image points, including the image end point, a respective distance of a second real point of the second plurality of second real points imaged by a second image point from a reference plane;

Determining a group of point pairs, which each contain a first image point from the first plurality of first image points and a second image point from the second plurality of second image points, which correspond to one another in such manner that the first and the second image point of a point pair image the same real point;

Determining a spatial position change of the viewing field of the image sensor on the basis of the group of point pairs;

Calculating measurement result information based on a first position of the image start point on the image sensor, a second position of the image end point on the image sensor, depth information for the image start point and/or the image end point, the imaging properties of the optical system and the spatial position change of the viewing field, wherein the measurement result information is a length or an area in the scene; and Outputting the measurement result information.

The determination of the spatial position change of the viewing field of the image sensor is based on recognizing that the spatial position of the viewing field can change in three degrees of freedom of translation, in particular x coordinate, y coordinate and z coordinate and in three degrees of freedom of rotation, in particular α angle, β angle, γ angle, so-called Euler angles or Cardan angles. Based on these six variables, it is possible to describe how, from a reference point of the image sensor, a determined real point, which is captured in the first spatial position of the viewing field with the coordinates (x, y, z), is then captured in the second spatial position of the viewing field with the coordinates (x', y', z'). Conversely, this means that if enough independent equations can be presented, the six variables, which describe the spatial position change, can be determined from identified resulting transformations of real points $p_n$ ($x_n, y_n, z_n$) in the first image to image points $p'_n$ ($x'_n, y'_n, z'_n$) in the second image. Thus, the spatial position change of the viewing field of the image sensor is determined on the basis of the group of point pairs.

It is thereby at least approximately assumed that the observed points or the observed object itself do or does not move. To this end, a pure affine transformation is used: $p'=R*p+t$, wherein p is the vector to a real point, whose coordinates are obtained using the first image, p' is the vector to the corresponding transformed real point, whose coordinates are obtained using the second image, t is a translation vector and R is a rotation matrix.

If the spatial position change is known, the positions of image start point and image end point, each including the respective depth information, can be converted into a common reference system. In the case of a preferred embodiment, the position of the image start point recorded in the first spatial position of the viewing field of the image sensor can thereby be converted into a transformed position, wherein this transformed position indicates the position in which the image sensor would have recorded the image start point and with what value its depth information would have been determined if the image start point would have been recorded in the second spatial position of the viewing field of the image sensor. Conversely, in the case of a further preferred embodiment, it is also possible to convert the position of the image end point recorded in the second spatial position of the viewing field of the image sensor into a transformed position, wherein this transformed position indicates the position in which the image sensor would have recorded the image end point and with what value its depth information would have been determined if the image end point would have been recorded in the first spatial position of the viewing field of the image sensor.

Since the reference points, i.e. the image start point and the image end point, are now indicated in a common reference system, calculations can be carried out on the basis of the position of the reference points, that is a measurement result information can be calculated in relation to the real start point and real end point. In the simplest case if the scene to be measured can be considered as substantially flat and parallel to the image plane, it is sufficient to consider the x and y positions of the reference points, i.e. in the image plane of the optical system. In order to now identify actual distances in the scene from the x and y positions in the image plane of the optical system, in addition to the depth information, here the distance of the image plane of the optical system from the scene, the imaging properties of the optical system must be known.

The imaging properties of the optical system include in particular the opening angle and the magnification factor or zoom factor. If these optical imaging properties of the optical system are known, the image point distances within an image can be converted in real point distances in the scene if the distance between image plane and plane of the scene is also known. The magnification factor or zoom factor of the optical system can for example be determined by detecting a manual actuating element for adjusting the magnification or the zoom, by detecting a motor position or motor actuation of the zoom; automatically adjusted by a connected camera control unit (CCU) or identified from an image. It can thus be found for example by way of calculation that in the case of determined imaging properties of an optical system and of a determined depth, the distance between the middle points of two adjacent image points of the image sensor corresponds to a distance of 0.1 mm in the scene. If it is thus identified that image start point and image end point in the common reference system have a distance of for example 124 image points, the corresponding actual distance in the scene is 124×0.1 mm=12.4 mm.

Using the known imaging properties of the optical system, it can be calculated taking into account the depth information which segment measured in image points corresponds to which segment in a unit of length in the scene.

If the scene to be measured cannot or should not be considered substantially flat and parallel to the image plane, the depth information of the image start point, i.e. a first distance of the real start point from the image plane, and the depth information of the image end point, i.e. a second distance of the real end point from the image plane, can additionally be taken into account. Preferably, the depth information of all or a large number of image points is continuously determined and used to calculate so-called depth maps.

In the case of some preferred embodiments, the depth information for at least one reference point, i.e. the image start point, the image end point or similar further points, for example an image sequential point, is obtained from the depth information of the nearest points. In this way, it is possible to assign depth information to such a reference point, even if this depth information could not be determined or could not be determined sufficiently accurately for this reference point. The depth information of the corresponding nearest point can thus be assigned to this reference point for example. Alternatively, an average value of the depth information can be formed from at least two nearest points and assigned to the reference point. If a plurality of nearest points are used, each of the nearest points with greater proximity to the corresponding reference point can be weighted higher. It should be pointed out that, in the same way, depth information can also be assigned to all image points, for which depth information could not be determined or could not be determined sufficiently accurately, such that an at least largely complete depth map is created for the image or all of the images.

The difference between the first spatial position and the second spatial position, which is different to the first spatial position, results from the image sensor or at least the viewing field of the image sensor being moved in a translational and/or rotational manner relative to the scene.

It is preferred when an image target point is displayed to the user, in particular as an overlay on a screen displaying a current image captured by the image sensor, wherein the image is in particular part of a continuous sequence of video images captured by the image sensor. This simplifies the correct positioning of the image target point as the image start or image end point for the user, wherein, when the first image is recorded, the image target point specifies the image start point and, when the second image is recorded, the image target point specifies the image end point. In the case of some embodiments, these reference points, i.e. the image start point and the image end point, can be selected to be different, by the image target point being repositioned between the recording of the first image and the recording of the second image. For example, the image target point in the shape of a cursor, cross hairs or the like, can be moved to a desired location, especially while viewing the live video image of the scene, by means of an input device such as a mouse, or a 3D mouse, for use with a hand or a foot. Alternatively, it can be placed on a touchscreen with a finger of the user. The image target point can therefore be made to align with a real start point or a real end point in the scene and in this manner select the image start point and the image end point that form the basis of the measurement calculation between the real points. In other words, the points are selected as measurement points. Concurrently, the image sensor can be repositioned relative to the scene. In the case of a preferred configuration, the reference points are fixedly predefined, which means that there are predefined image points on the image sensor. The reference points (image start point and image end point) can thereby in particular be identical. This can facilitate handling since, by changing the spatial position of the image sensor, in particular of the instrument, for example an endoscope, in which the image sensor is arranged, or by adjusting the viewing field of the image sensor, the user moves the image target point to overlap with the desired real point which is represented in the image. Therefore, the instrument comprising the image sensor becomes the input device. The respective image is then recorded in order to thus specify or define the respective reference point or the real start and real end points for the respective recording, which are the basis for calculating the measurement result information. In the case of a preferred configuration, the image target point is selected as the image center of the image sensor. The selection of points for measurement preferably takes place while a video image of the scene is displayed to the user in real time. The user can thus easily and intuitively select the desired points in different images. Selecting real start points and real end points between which the measurement result information is to be calculated can, for example, be done by pressing a button or by triggering a signal on the input device in another way.

The image sensor can be sensitive to light in the visible range. It is also possible that additionally or alternatively to this, the image sensor is sensitive to light in the near-infrared range, which in particular makes it possible to observe fluorescence. In the case of some configurations, the image sensor is an element of a video endoscope, a video exoscope or a video microscope both for medical and for non-medical or technical use.

The spatial position, also referred to as pose, refers to the combination of position and orientation of an object. Three degrees of rotational and translational freedom can therefore be described via the spatial position.

The reference plane can be freely selected by the person skilled in the art since the determination of the spatial position change of the viewing field of the image sensor is based on a relative change of real points, as perceived by the image sensor. Thus, it is in particular possible to consider the image plane of the optical system or a plane parallel to this image plane as a reference plane.

The image sensor can in particular be a monosensor, which generates exactly one image of the scene, or a stereo sensor, which generates two different images of the scene. The stereo sensor can have a continuous light-sensitive area, which records, in a first region, a left image or partial image of the scene and, in a second region, a right image or partial image of the scene. The stereo sensor can also have two light-sensitive areas and circuit boards separate from one another, wherein one area records a left image or partial image of the scene and the other area records a right image or partial image of the scene. The separated light-sensitive areas can thereby each be arranged in one of two completely separate sensors.

The determination of the point pairs can take place by means of known methods for image registration, thus for example by means of ORB, SIFT or SURF, see for example the publication Image Matching Using SIFT, SURF, BRIEF and ORB: Performance Comparison for Distorted Images" by Ebrahim Karami, Siva Prasad, and Mohamed Shehata, Faculty of Engineering and Applied Sciences, Memorial University, Canada, as well as the publications cited therein.

The term, spatial position change of the viewing field of the image sensor, should be understood to the extent that both the case of a rigid optical system and the case of an optical system with variable viewing axis or viewing direction, for example through a prism or adjustable mirror, are intended to be covered. In the case of a rigid optical system, a spatial position change of the image sensor arranged fixedly thereto also leads directly to a spatial position change of the viewing field of the image sensor. The term, spatial position change of the viewing field of the image sensor, then means a spatial position change of the image sensor. In the case of an optical system with variable viewing axis, the viewing field can be changed without the spatial position of the image sensor having to change. Thus, for example the spatial position of the viewing field can be changed for example by displacing a prism or a mirror along the beam path without the spatial position of the image sensor changing.

In practice, it has been shown that, in the case of a full HD resolution (1920×1080 pixels) in the first image and in the second image, many hundreds or thousands of distinctive locations, such as edges or contrast-rich regions, can be automatically identified. 100 locations in the first image can be assigned to roughly 100 locations in the second image for example by means of a comparison of the first and second image. If it is further considered that in particular image points remote from one another promise a high probability of a linear independence in regard to the spatial position change to be determined, around 30 to 50 point pairs should normally be expected, which allows for a good determination, at least approximately, of the six variables. Corresponding, optimizing algorithms, in order to estimate the rotation and translation, are known to the person skilled in the art, e.g. RANSAC algorithms.

When determining the spatial position change, prior knowledge is preferably used e.g. if one degree of freedom is fixed due to an outer boundary condition and/or a first degree of freedom is in a defined dependency in relation to at least one second degree of freedom. Thus, there can be determined boundary conditions for the movement of the instrument, e.g. if the image senor is part of a rigid instrument, which inserts in a trocar. The image sensor can then only be displaced along the trocar shaft and, since the trocar is introduced into the cavity to be examined through a small opening, which therefore represents a pivot point for the trocar, any pivoting of the image sensor also directly results in a defined translation. Therefore, known fixing points or restrictions of the degrees of freedom can be taken into account in order to improve and simplify the calculation of the movement or check for plausibility. Alternatively or additionally, data can be used by a movement sensor, as will be explained in more detail below.

Furthermore, the information regarding the determined spatial position change can be used in order to improve the continuously generated depth map of the scene or check for plausibility. Thus, values for different real points of the depth maps previously generated in the method can be transferred to the respectively current reference system using the identified rotation and translation. Average values can be formed from a plurality of such depth values for a real point and uncertainties, e.g. the standard deviation, can be determined. In this way, it is possible to check the quality of the identified depth values. Depth values missing in the current image, i.e. the current depth map, can thus also be derived, if required, from previous values and automatically added.

Prior knowledge, such as e.g. regarding a pivot point or measurement data from an inertial sensor, changes the above-described affine transformation. Thus, for example in the case of a pivot point, the possible degrees of freedom of the movement of the optical visualization system or of the viewing field of the image sensor are reduced from six to four since it can now only be rotated in a left to right, up to down, in to out direction and about its own axis. As a result, fewer parameters need to be identified by the RANSAC method such that the result is more stable. In the case of one embodiment, the measurement data of one inertial sensor is used to determine the rotation matrix. Therefore, only the three degrees of freedom of the translations have to be determined. In the case of another embodiment, the inertial sensor data is used as an initialization value for the rotation matrix in an iterative search for the parameters of the movement.

One aspect of the disclosed measuring method is based on the idea that a simple measuring function is possible for size and dimension determination in a scene, in particular with an anatomical structure, by purely optically capturing the scene such that navigation systems and other sensors, such as for example position sensors, can be dispensed with.

This can be achieved by a first image and a second image of the scene, in particular with the anatomical structure, being recorded by means of the image sensor. The first image and the second image are hereby recorded from different spatial positions of the viewing field of the image sensor. This means that the orientation, the position, the distance and/or the direction from which the image sensor records images of the scene changes between the recording of the first image and the recording of the second image. The recording of the images also takes place by the same image sensor, which, as previously explained, can have two light-sensitive areas separate from one another. The image sensor is preferably part of a stereo-video endoscope with built-in, separate, distal and proximal light-sensitive areas. Alternatively, the image sensor can be part of a microscope or exoscope.

The measurement does not take place, as already known from the state of the art, in a static image, in which two measuring points are selected automatically or by a user, but rather the image sensor, at least the viewing field of the image sensor, is displaced manually or automatically, therefore two different images can be recorded from two different spatial positions in which image start and end points and corresponding real start points and real end points can be defined for determining the measurement result information. The images are part of a video sequence of the scene displayed to the user in real time or approximately in real time. Such a video sequence can, for example, have a 4K resolution and be displayed with at least 30 fps (frames per second). Therefore, it is possible to robustly determine, in real time, the actual distance of two real points recorded at different times and in different images, even though the position of the image sensor changes in the meantime.

In particular, the present method makes it possible to identify measurement information between real points, which are not in the viewing field of the image sensor at the same time. Image start and image end point can thus be selected such that the measurement takes place between points which are not visible to the user at the same time, for example because the structure to be measured is too large. To this end, depth information for a plurality of points and rotation and translation of the image sensor can be identified continuously from point pairs in different images, if required.

As explained, a spatial position change of the viewing field of the image sensor is determined on the basis of the group of point pairs which are obtained from the first and the second image. The spatial position change can, however, also be identified on the basis of further groups of point pairs, as will be explained below on the basis of a preferred configuration.

It is understood that the measuring method is suitable not only for intraoperative examinations, but also for example suitable for examining the oral cavity of a patient. Furthermore, cursory medical examinations are possible in which a simple determination of lengths or areas is desired.

In the case of a preferred configuration, the measuring method also has the following steps:

Recording a third image of the scene, wherein recording takes place using the image sensor, in the third image, a third plurality of third image points image a corresponding third plurality of third real points of the scene by means of the image sensor and an image sequential point of the third plurality of third image points defines a real sequential point in the scene, wherein, when the third image is recorded, the viewing field of the image sensor is located in a third spatial position relative to the scene, which differs from the first and the second spatial position;

Identifying third depth information which describes, at least for a third subset of the third plurality of third image points, including the image sequential point, a respective distance of a third real point of the third plurality of third real points imaged by a third image point from the reference plane;

Determining a further group of point pairs, which each contain a second image point from the second plurality of second image points and a third image point from the third plurality of third image points, which correspond to one another in such manner that the second and the third image point of a point pair image the same real point;

Determining a further spatial position change of the viewing field of the image sensor on the basis of the further group of point pairs;

wherein calculating the measurement result information is also based on a third position of the image sequential point on the image sensor, the third depth information and the further spatial position change of the viewing field or further measurement result information is calculated based on a third position of the image sequential point on the image sensor, the third depth information and the further spatial position change of the viewing field.

This configuration also makes it possible to capture further reference points, which should be taken into account for determining a length, for example of a multi-part path, or an area, for example of a polygon. It is also possible that the mentioned first real sequential point and image sequential point are followed by a second real sequential point, which can in turn be followed by a third real sequential point and image sequential point, etc. In this case, a group of point pairs with corresponding points are identified between successive real sequential points or image sequential points, i.e. an nth and a (n+1)th real sequential point or image sequential point, from which in turn a respective nth spatial position change of the viewing field of the image sensor is identified on the basis of the group of point pairs. Therefore, complex paths and polygons can also be captured. In the case of a preferred embodiment, the real sequential point or the real sequential points can be selected by a user action, as will be explained in more detail below. In the case of another preferred embodiment, the real sequential points are captured continuously with each spatial position change of the viewing field of the image sensor such that just by guiding the instrument, in which the image sensor is integrated, a length can be captured and identified, for example if a path is departed.

In the case of a preferred configuration, the following steps are carried out before recording the second or the third image:

Recording at least one intermediate image such that a sequence is formed beginning with the first image, continued over the at least one intermediate image and ending with the second or the third image, wherein, in each intermediate image, a further plurality of further image points image a corresponding further plurality of further real points of the scene by means of the image sensor and wherein, when the intermediate image is recoded, the viewing field of the image sensor is located in a further spatial position relative to the scene, which differs from the previous spatial position within the sequence;

after recording an intermediate image of the at least one intermediate image:

Identifying further depth information, which describes, at least for a further subset of the further plurality of further image points, a respective distance of a further real point of the further plurality of further real points imaged by a further image point from the reference plane;

Determining an intermediate group of point pairs, which each contain a first sequence image point from the further plurality of further image points in the intermediate image and a second sequence image point in a previous image from the sequence, which correspond to one another in such manner that the first and the second sequence image point of a point pair image the same real point; wherein the spatial position change or the further spatial position change is also determined on the basis of the at least one further intermediate group of point pairs.

As previously explained, it is possible to identify the spatial position change from the information regarding the first image and the second image without the real start point and the real end point having to be imaged at the same time in one of these two images. Accordingly, the further spatial position change can be identified from the information regarding the second image and the third image without the real end point and the real sequential point having to be imaged at the same time in one of these two images.

The position change can essentially, however, be so great that it is difficult or impossible to determine the group of point pairs or the further group of point pairs. The preferred configuration takes this into account by at least one intermediate image and preferably a plurality of intermediate images being created while the spatial position is changed. This forms a sequence of images.

On the basis of the processing of an image from the sequence and a previous image of the sequence, a position change can be identified which has taken place between the recording of the image and of the previous image. This processing takes place in principle just like the processing of first and second image or of second and third image. Therefore, it is possible to identify segments of the position change with images from the sequence and thus to identify the entire position change between first and second image or second and third image from the segments.

This configuration makes it possible to precisely determine the spatial position change or the further spatial position change even over larger distances.

In the case of a further preferred configuration, at least one part of the first and second depth information is obtained from stereo information.

Different known methods can thereby be used, such as for example those described in the bachelor thesis by Christian Blank, titled "Generierung von Tiefenbildern mittels Stereoskopie", submitted on 13 Sep. 2013 and cited in the bibliography. In the case of some embodiments, the stereo image of the scene is generated by means of a stereo instrument, more precisely, a left image or partial image of the scene and a right image or partial image of the scene, and from the disparity between the two images of the stereo image and further information, the depth information for many image points is continuously determined from the stereo image. Corresponding points in the left and the right image can in particular be determined by semi-global (block) matching, as is described in the publication, "Accurate and efficient stereo processing by semi-global matching and mutual information", Heiko Hirschmüller, IEEE Conference on Computer Vision and Pattern Recognition, 2005, or in the publication "Semi-Global Matching: Motivation, Development and Applications", Heiko Hirschmüller, Photogrammetric Week, September 2011. Depth information is obtained therefrom for many image points, in particular a depth map. A depth sensor, which is based on a time-of-flight (ToF) measurement, is thereby not necessary. It should be pointed out that pseudostereoscopy and pseudostereo image fall under the terms stereoscopy and stereo image. The pseudostereoscopy technique uses successive images from an instrument that has no stereo sensors.

The depth information can be determined in the case of one embodiment using the following formula: Depth (in a unit of length)=stereo base (in the unit of length)*focal length (in pixels)/disparity (in pixels). This is calculated using pixels. The focal length in pixels is identified according to known methods. It can be determined in particular on the basis of a defined checkerboard pattern at a defined distance. From the depth and the angle information, the x and y component is also then calculated, wherein the x and y component can be in a unit of length. The angle information can thereby be obtained from calibrating the optical system, e.g. using a checkerboard.

In the case of one embodiment, camera parameters are incorporated into a calibration of the measuring method determined at the beginning. This links, among other things, the disparity to the depth. The calibration is dynamically adapted to the camera settings. A magnification or a digital zoom can be taken into account when calculating the calibration. For example, a magnification by the factor two means that the disparity doubles with constant depth.

A particularity of this configuration is also that the image start point, the image end point and any other corresponding image points can be represented on a 3D screen when using a stereo instrument, which has a stereo sensor. To this end, the assigned disparity, i.e. the offset of the corresponding image points on the left and the right image or partial image, is read for each image point and the positions of the set points, in particular the image start point and the image end point and any represented measuring lines in the first image is displaced by the corresponding number of pixels compared to the second image. A disparity is thus also generated for the set points, which can be displayed with an overlay, and any measuring lines and areas, including the image target point, such that they appear to the observer on a 3D screen at the correct distance. The points and lines can be represented either in one plane or superimposed such that they appear to lie on the surface of the observed structure. Measuring lines and points can therefore be displayed either in the foreground in a plane with identical depth or at the actual depth of the selected structures in the represented scene. In particular, measuring lines can run between image start and image end points for the observer at the depth along contours of imaged structures. With the described method a real start point or a real end point can be defined as a measurement point and marked, for example via an overlay on the current video image, and when changing the position of the image sensor the marking can automatically be moved along such that the measurement point will still be displayed as being assigned to the real point, despite the movement of the image sensor and the change of perspective. The measurement point therefore appears to be glued to the scene and to an object's surface at the correct position and in the correct depth. Measurement lines between two points can be displayed in the same manner while the image sensor is moved.

In the case of the present method, the left and right image are, to this end, rectified in particular before determining the depth information, i.e. the disparities and the depth map. Rectification means that distortion effects of the optical system and possible rotary arrangement of the image sensors in relation to one another are corrected in the images by way of calculation and removed and the images are aligned parallel to one another. Then, as previously described, the disparity values for different image points and therefore the depth information or the depth map are identified. The image start point or image end point is selected, for example using the image target point, e.g. by the user, in a non-rectified partial image, for example the left image, and then its coordinates are transferred to the rectified geometry. Then, the disparity value for the relevant point is read. The relevant measuring point is now displaced in the assigned right image by the read disparity in pixels and transformed back again from the rectified to the normal image geometry and superimposed in the image. Thus, the relevant point in the stereo image is seemingly represented at the suitable distance, for example on the surface of a structure. A point appears at a greater depth when the disparity is reduced and at a shallower depth when the disparity is increased.

If, instead, all image start and image end points are supposed to be represented in one plane at the same depth, all points can be set to the maximum occurring disparity and then appear in the foreground in front of the observed structure. However, if necessary, it is also possible to represent the measuring points and lines in a 2D image.

The approach can be similar for superimposed segments, numerical values, areas, etc., such that they are superimposed at the correct depth in the 3D image.

It should be pointed out that the general knowledge and methods for stereoscopy, as described and referenced for example in "Stereoskope HD Produktionen—Messungen statt Mythen", Editor Nikolaus Hottong, Publication series Digital Media Faculty of HFU Furtwangen University, December 2016, ISBN 3-9810384-9-5, are assumed to be known and are not explained further here.

In the case of a further preferred configuration, the measurement result information includes a distance between the real start point and the real end point.

As previously explained, spatial coordinates of the reference points can be determined based on the positions of the reference points, i.e. of the image start point and of the image end point, and of the respective depth information. This makes it possible to calculate the distance between the real start point and the real end point using the normal Euclidean distance formula.

In the case of a further preferred configuration, the measurement result information includes a segment along a contour between the real start point and the real end point.

In the case of this configuration, it is assumed that on the basis of image processing, a contour can be identified, which begins at least in proximity to the real start point and ends at least in proximity to the real end point. The segment can then be identified by support points along the identified contour, wherein the support points, if necessary, are transformed into the reference system of the reference points.

In the case of a further preferred configuration, the measurement result information includes an area, whose boundary is identified taking into account the real start point and the real end point.

In the case of this configuration, it is assumed that a closed contour is determined by the real start point and the real end point, for example a circle by middle point and radius or by two circular arc points or a rectangle by two opposing corners. If the scene can be considered substantially flat, the area can be simply calculated with suppression of the depth information in the two-dimensional image. If the depth information is also supposed to be processed, the contour can be broken down into primitives, whose areas are then added to an overall area. By using three points, in particular real start point, real end point and real sequential point, the area of a thus defined triangle can for example be calculated. If a plurality of real sequential points are available, the area of polygons can also be calculated.

In the case of a further preferred configuration, at least one part of the first and second depth information is obtained from time-of-flight information provided by the image sensor or a depth image sensor.

In the case of this configuration, at least one part of the depth information is identified by the image sensor or a depth image sensor, which also captures the scene at least in relation to the real start point and the real end point. Thus, depth information of the first recorded image and of the second recorded image can be determined by recording a depth image of the viewing field of the image. In this case, different types of distance and depth measurements are possible in order to identify the depth information. Examples are ultrasonic measurements or laser distance measurements (LIDAR). Additionally, the depth image sensor may be a time-of-flight camera. In this case, short light pulses, which are then reflected by the scene, are emitted with an illumination unit, which preferably has one or a plurality of LEDs or laser diodes and which is actuated in a modulated manner. An optics receives the reflected light and images the recorded scene. Since a depth image sensor generally has a lower resolution than a general image sensor or white light image sensor, respective depth information can be assigned by interpolation to further points between the measured points of the depth image in the case of one embodiment.

In the case of a further preferred configuration, at least one part of the first and second depth information is obtained from focus information of the optical system.

Such optical systems can have a focus with a fixed focus length. Since the user will thus select the distance of the image sensor from the scene such that the scene is represented at least roughly sharply, the focus length can be used when determining the first and/or second depth information or used as the first and/or second depth information. This can take place for one part or for all image points of the first and/or second subset. If the optical system has a manual actuating unit for changing the focus length, the current focus length can be identified by position detection of the actuating unit. If the optical system has a motorized actuating unit for changing the focus length, the current focus length can be identified by position detection of the motor of the actuating unit.

In the case of a further preferred configuration, the first and/or the second image is recorded by a user action. Alternatively, the defining a real start point and a real end point is triggered by a user action.

This configuration offers particularly simple and intuitive operation. In this case, the image from the image sensor is shown to the user on a screen, in particular as a continuous sequence of video images, e.g. 25, 30, 50 or 60 images per second, with a visually highlighted image target point, e.g. a cross-hair. For example, the user moves the image target point to overlap with a desired real start point, which is represented in the image of the image sensor, or chooses the image start point in a different manner as described before, and triggers the recording of the first image or the defining of a real start point as a measurement point, e.g. by a user action, in particular by means of pushing a button, a touch, a keystroke, a head or hand gesture or a voice command. The choosing and defining a real start point or real end point can be done with a single combined user action. Then, by moving the image sensor or by changing the position of the viewing field of the image sensor, the user moves the image target point with a desired real end point, which is represented in a further image of the image sensor, to overlap and triggers the recording of the second image or the defining the real end point by a further user action. The defining a real start point or a real end point for measurement can include saving the coordinates of the real point or of the corresponding image point and a corresponding depth information in a memory or include the marking of the selected point in the image for example using a graphical overlay in the form of a visible measurement point.

In the case of a further preferred configuration, the spatial position change of the viewing field of the image sensor is determined taking into account movement data, which is recorded by a movement sensor arranged stationary relative to the image sensor.

The movement sensor is preferably an acceleration sensor, which is calibrated at the beginning and provides information about accelerations in x, y and z direction resulting from acting forces. The acceleration sensor registers the movements and by double integration of the acceleration, a quantitative value is obtained for the movement of the acceleration sensor. The position of the sensor with respect to the gravitational axis can be indicated e.g. in angles. The reliability of this measurement can be further increased by further sensors, e.g. such as a magnetometer, being installed together with the gyroscope installed in the acceleration sensor. Any errors that occur when determining the movement data can be compensated by corresponding filtering, such as e.g. by a Kalman filter or a high-pass filter. In the case of some configurations, the movement sensor is integrated in the image sensor or arranged on the image sensor.

The movement data can preferably be used to at least partially correct or compensate uncertainties or implausible values when identifying the spatial position change on the basis of the group of point pairs. If a value or a plurality of values of the identified spatial position change indicate that the spatial position change has been identified incorrectly, the movement data can replace values of the spatial position change. In the case of uncertainties, for example if different partial groups of point pairs, which are used for identifying the spatial position change, lead to significantly different identified spatial position changes, the movement data can be taken into account in a weighted manner such that the determination of the spatial position change of the viewing field of the image sensor takes place on the basis of the group of point pairs with a first weight and the movement data with a second weight. Additionally, it is possible to check the plausibility of the movement data against the group of point pairs and vice versa.

In the case of a further preferred configuration, the calculation of the measurement result information includes a first calculation of first coordinates of the real start point in a unit of length and a second calculation of second coordinates of the real end point in the unit of length and wherein the measurement result information is calculated on the basis of the first and second coordinates.

The calculation of the coordinates in a unit of length, i.e. for example as (23 mm, 8 mm, 15 mm), makes it possible to further process and calculate the measurement result information in a particularly simple manner. The origin of such a coordinate system is here, as with the other configurations, preferably selected at the distal end of the optical visualization system or instrument with at least one image sensor in the middle of the stereo base.

In the case of a further preferred configuration, at least one region of the scene captured by the image sensor is illuminated at least temporarily with a pattern.

The illumination with a pattern or with structured light is in particular advantageous as an extension to the stereo construction. In this case, an inhomogeneous, time-variable illumination is performed of an endoscopic scene, in which the anatomical structure to be measured is located. A significant advantage resulting from this is that a reliable stereo construction is therefore also possible in low-contrast situations. In terms of time, such inhomogeneous illumination, for example using a matrix LED, can be actuated very quickly (~1000 Hz) such that the observer still has a homogeneous illumination impression due to the corresponding selection of the viewing pattern. It is in particular thereby advantageous if the measuring device has a light source with a plurality of individually actuatable individual light sources to illuminate the viewing field of the image sensor and a control unit configured to control the individual light sources in such manner that an inhomogeneous and time-variable illumination of the viewing field of the image sensor is achieved.

According to a further aspect, the object is achieved by a measuring device, having an image sensor, in front of which an optical system is arranged; and a processor designed to carry out the steps of a measuring method previously described. The processor thereby actuates the image sensor to record images. Optionally, the processor can also actuate a light source.

In the case of an advantageous configuration, the measuring device also has a light source designed to illuminate at least one region of the scene captured by the image sensor at least temporarily with a pattern.

It is understood that one exemplary aspect can also be any combination of the dependent claims with the respective independent claim. A redundancy of the dependent claims for the respective independent claims is therefore deliberately avoided.

It is also understood that the claimed measuring method and the claimed measuring system have similar, corresponding and/or identical preferred embodiments, in particular as defined in the dependent claims and as disclosed herein.

BRIEF DESCRIPTION OF THE DRAWINGS

Further advantageous embodiments are defined below.

The exemplary embodiments will be explained in more detail below on the basis of the drawings, in which is shown.

DETAILED DESCRIPTION

Figure 1:
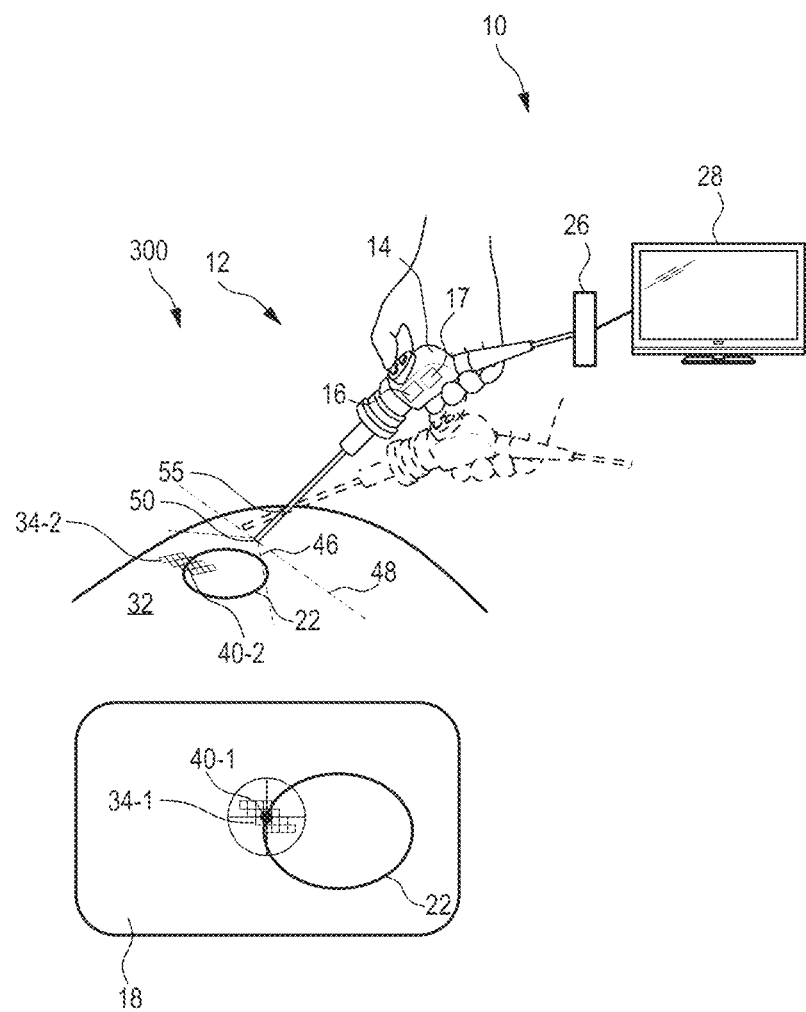
FIG. 1 is a schematic representation of an embodiment of a measuring system with a viewing field of an image sensor in a first position.

FIG. 1 shows a schematic representation of an exemplary endoscopic measuring device 10 connected to an endoscope 12, on which a camera 14 with a symbolically represented image sensor 16 is arranged. The image sensor 16 has two separate imaging areas in order to generate a left image and a right image for stereoscopy. An optional movement sensor 17 is arranged stationary in relation to the image sensor 16 and captures a displacement of the image sensor 16.

Figure 2:
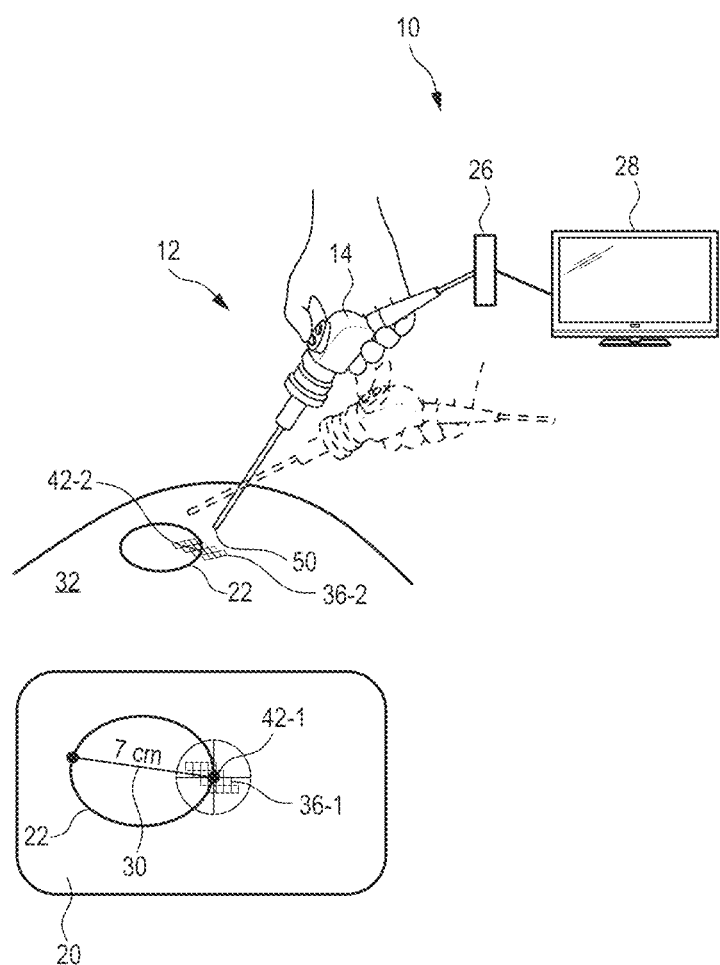
FIG. 2 is the schematic representation from FIG. 1 with the viewing field of the image sensor in a second position.

In connection with FIG. 2, it can be discerned that a first image 18 and a second image 20 of an anatomical structure 22 are recorded by means of the image sensor 16. The image sensor 16 is preferably an element of a video camera. The endoscope 12 can preferably be coupled to an illumination unit which illuminates a scene 32 to be examined via light guides in the interior of the endoscope 12 at a distal end 50 of the endoscope 12. An optical system 55 is arranged between the image sensor 16 and the distal end 50 in the interior of the endoscope 12.

The anatomical structure 22, which is imaged in the recorded images 18, 20 is only shown by a schematic oval representation. Real recordings of an anatomical structure 22 to be examined are e.g. shown in the FIGS. 5, 7 and 11. The structure 22 to be examined can for example be an aneurysm, a tumor or another anatomical structure.

By comparing the images 18 and 20, it is clear that the first image 18 and the second image 20 have been recorded from different positions since the anatomical structure 22 is displaced to the left in the second image 20 relative to the first image 18. This means that the spatial position, i.e. the distance and/or the orientation and/or the direction, from which the image sensor 16 records images of the anatomical structure 22, changes between the recording of the first image 18 and of the second image 20. This change can for example take place manually by a user, as is shown in FIGS. 1 and 2 by dashed lines, or by a robot.

The images 18, 20 recorded by the image sensor 16 will be transferred to a processor 26. The processor is preferably integrated in a computer and designed to carry out the measuring method according to an embodiment, see FIG. 4, to calculate the measurement result information, preferably a size determination of the anatomical structure 22. The processing of the recorded images 18, 20 can take place via a camera control unit (CCU). Similarly, fast processing is possible via a FPGA.

After the recorded images 18, 20 are processed by the processor 26, the images are displayed on a display device 28, as is normal in endoscopy. The display preferably takes place in combination with measurement result information 30, which has been previously calculated by the processor 26. This measurement result information 30 can, as is shown in FIG. 2 by way of example, be the length of the anatomical structure 10, here 7 cm.

Figure 3:
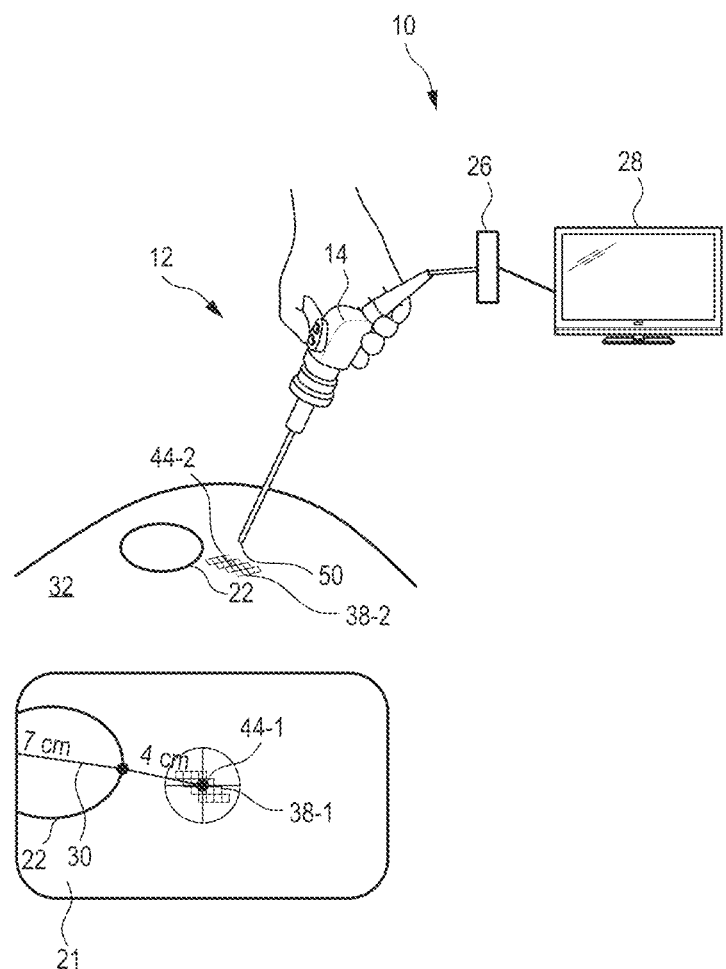
FIG. 3 is the schematic representation from FIG. 1 with the viewing field of the image sensor in a third position.
Figure 4:
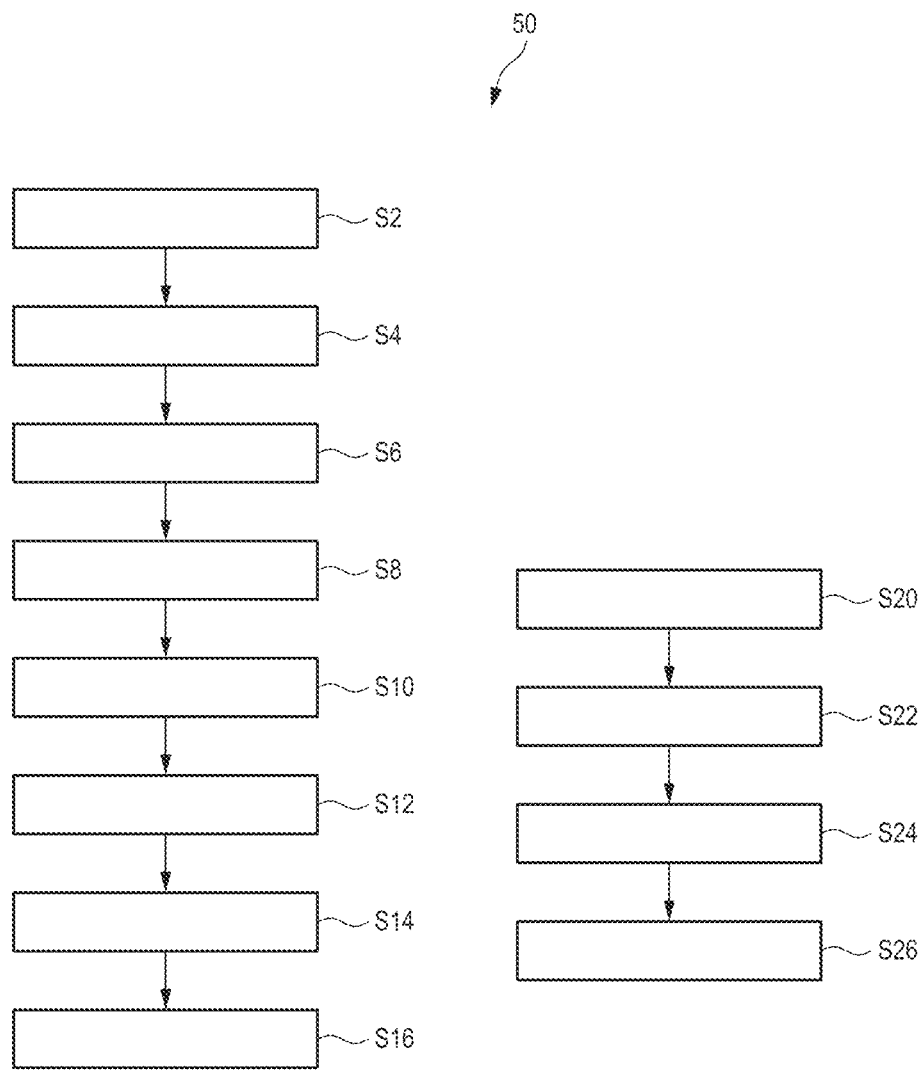
FIG. 4 is a two flow diagrams for schematically representing an embodiment of a measuring method.

FIG. 4 shows, in an overview with FIGS. 1 to 3, an exemplary embodiment of a measuring method 50. A first image of a scene 32 is recorded in step S2. This recording S2 takes place using the image sensor 16, in front of which the optical system 55 is arranged, wherein, in the first image 18, a first plurality of symbolically represented first image points 34-1 image a corresponding first plurality of symbolically represented first real points 34-2 of the scene 32 by means of the image sensor 16. A symbolically represented image start point 40-1 of the first plurality of image points 34-1 defines a real start point 40-2 in the scene 32, wherein, when the first image 18 is recorded, a viewing field 46 (indicated by two dashed lines) of the image sensor 16 is located in a first spatial position relative to the scene 32.

In step S4, first depth information is identified which describes, at least for a first subset of the first plurality of first image points 34-1, including the image start point 40-1, a respective distance of a first real point 34-2 of the first plurality of first real points 34-2 imaged by a first image point 34-1 from a reference plane 48 (represented symbolically with a dot-dashed line).

In step S6, a second image 20 of the scene 32 is recorded, wherein the recording S6 takes place using the image sensor 16. In the second image 20, a second plurality of symbolically represented second image points 36-1 image a corresponding second plurality of symbolically represented second real points 36-2 of the scene 32 by means of the image sensor 16. An image end point 42-1 of the second plurality of second image points 36-1 defines a real end point 36-2 in the scene 32. When the second image 20 is recorded, the viewing field 46 of the image sensor 16 is located in a second spatial position relative to the scene 32, which differs from the first spatial position.

In step S8, second depth information is identified which describes, at least for a second subset of the second plurality of second image points 36-1, including the image end point 42-1, a respective distance of a second real point 36-2 of the second plurality of second real points 36-2 imaged by the second image point 36-1 from the reference plane 48.

In step S10, a group of point pairs is determined, which each contain a first image point 34-1 from the first plurality of first image points 34-1 and a second image point 36-1 from the second plurality of second image points 36-1, which correspond to one another in such manner that the first and the second image point 34-1, 36-1 of a point pair image the same real point 34-2.

In step S12, a spatial position change of the viewing field 46 of the image sensor 16 is determined on the basis of the group of point pairs.

In step S14, measurement result information 30 is calculated based on a first position of the image start point 34-1 on the image sensor 16, a second position of the image end point 36-1 on the image sensor 16, depth information for the image start point 40-1 and/or the image end point 42-1, the imaging properties of the optical system 55 and the spatial position change of the viewing field 46, wherein the measurement result information 30 is a length or an area in the scene 32.

Lastly, in step S16, the measurement result information 30 is output, in particular on the display device 28.

The measuring method 50 can include further steps, which can follow step S12, i.e. before the measurement result information 30, is calculated S14 and output S16, or can follow step S16, wherein after the measurement result information 30 has been calculated S14 and output S16, modified or expanded measurement result information is calculated and output.

In step S20, a third image 21 of the scene 32 is recorded, wherein the recording S20 takes place using the image sensor 16. In the third image 21, a third plurality of third image points 38-1 image a corresponding third plurality of third real points 38-2 of the scene 32 by means of the image sensor 16. An image sequential point 44-1 of the third plurality of third image points defines a real sequential point 44-2 in the scene 32, wherein, when the third image 21 is recorded, the viewing field 46 of the image sensor 16 is located in a third spatial position relative to the scene 32, which differs from the first and the second spatial position.

In step S22, third depth information is identified which describes, at least for a third subset of the third plurality of third image points 38-1, including the image sequential point 44-1, a respective distance of a third real point 38-2 of the third plurality of third real points 38-2 imaged by a third image point 38-1 from the reference plane 48.

In step S24, a further group of point pairs is determined, which each contain a second image point 36-1 from the second plurality of second image points 36-1 and a third image point 38-1 from the third plurality of third image points 38-1, which correspond to one another in such manner that the second and the third image point 36-1, 38-1 of a point pair image the same real point 36-2.

In step S26, a further spatial position change of the viewing field 46 of the image sensor 16 is determined on the basis of the further group of point pairs.

Calculating, step S14, the measurement result information 30 can now also be based on a third position of the image sequential point 44-1 on the image sensor 16, the third depth information and the further spatial position change of the viewing field 46 or further measurement result information 30 is calculated based on a third position of the image sequential point 44-1 on the image sensor 16, the third depth information and the further spatial position change of the viewing field 46.

Figure 5:
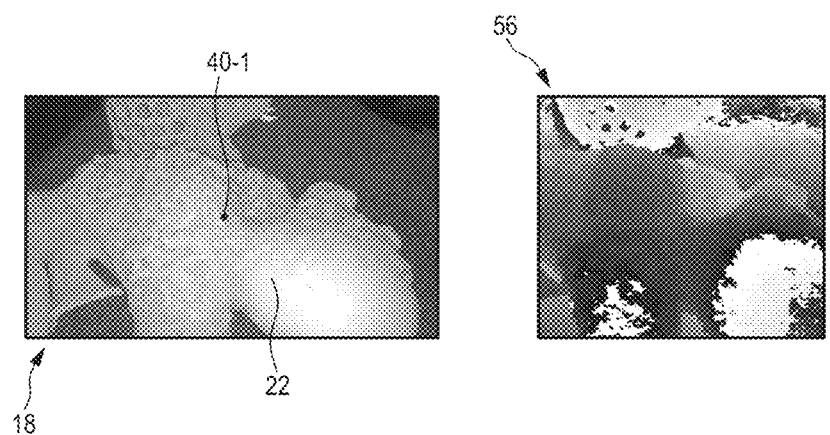
FIGS. 5 and 6 are image recordings and corresponding depth maps of an anatomical structure.
Figure 6:
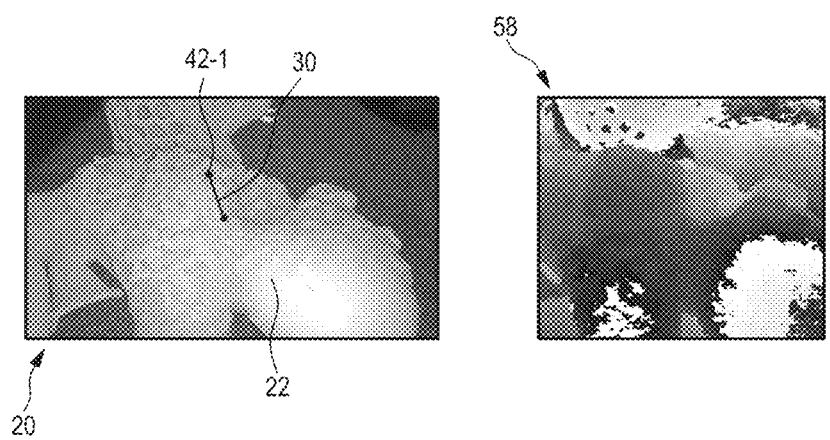

FIGS. 5 and 6 show image recordings and corresponding depth maps 56, 58 of an anatomical structure 22. The depth maps 56, 58 are examples of depth information 40 according to one embodiment.

FIG. 5 shows a first image 18 of the anatomical structure 22 (left) and an associated identified depth map 56 (right). FIG. 6 shows a second image 20 of the same anatomical structure 22 (left) and an associated identified depth map 58 (right). As is shown in FIGS. 1 and 2, the images 18, 20 are for example recorded using the image sensor 16 of an endoscope 12 and this endoscope 12 is moved in a translatory and/or rotary manner manually or by means of a robot between the recording of the first image 18 and of the second image 20. Then, the anatomical structure 22 is observed in the two images 18, 20 from different positions. This results in another feature of the anatomical structure 10 being seen in the image centers of the first image 18 and of the second image 20.

The corresponding depth maps 56, 58 can for example be identified via the disparity between the two images of the image sensors of a stereo endoscope or between the image sensors of a stereo endoscope or using a depth image sensor, such as a time-of-flight camera. Using the depth maps 56, 58, it is possible to determine 3D coordinate points for which the x, y and z coordinates are known based on the identified depth information. As already mentioned, the two images can also be obtained by pseudostereoscopy.

In the first image 18, the real start point 40-2 is thus determined by selecting the image start point 40-1, here in the middle point of the first image 18 and identifying the z coordinate via the corresponding depth map 56. In the second image 20, the real end point 42-2 is determined by accordingly selecting the image end point 42-1 and identifying the z coordinate via the corresponding depth map 58. It should be noted that this is only an example. The identification of complete depth maps is essentially not necessary since the depth information regarding the image start point 40-1 and the image end point 42-1 is sufficient to determine the real distance of two features of the anatomical structure 22.

The recorded images 18, 20 are preferably full HD images with a resolution of 1920×1080 pixels or 4K images with a resolution of 3840×2160 pixels. It may be thereby advantageous if each of the real start point 40-2 and the real end point 42-2 are selected in the image center at the pixel position (960, 540) after the endoscope 12 has been displaced.

After determining the first 3D coordinates for the real start point 40-2 and the real end point 42-2, measurement result information 80, such as for example the distance between real start point 40-2 and real end point 42-2, can be calculated. As can be seen in FIG. 6, this calculated distance is then displayed in the second image 20. The images 18, 20 are preferably individual frames of a video, which is recorded for example with a video endoscope during a medical examination.

Figure 7:
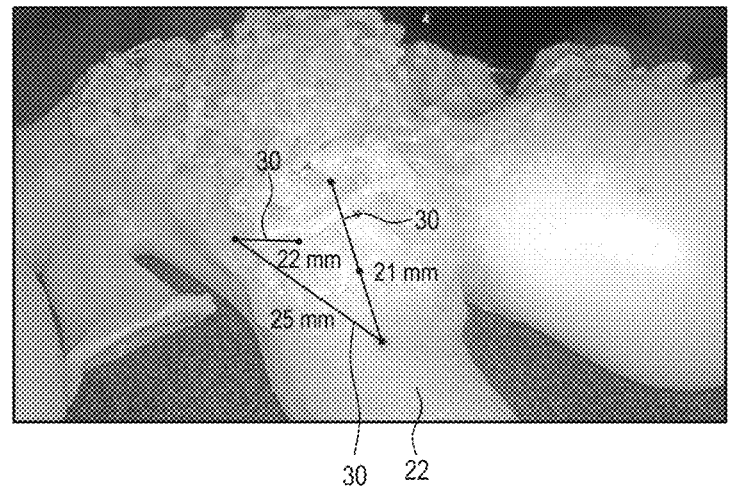
FIG. 7 is a further image recording of an anatomical structure.

FIG. 7 shows a further image recording of an anatomical structure 22 after applying the measuring method according to one embodiment. It can be seen that by way of the measuring method according to one embodiment, a plurality of distances (10 mm, 21 mm and 25 mm) between different features of the anatomical structure 22 can be calculated and displayed via the image sequence of a plurality of images. The medical specialist personnel are therefore capable of determining the dimension of the anatomical structure 22 reliably via different distance measurements. Optionally, uncertainties in the identified distances can be indicated with a standard deviation.

Figure 8:
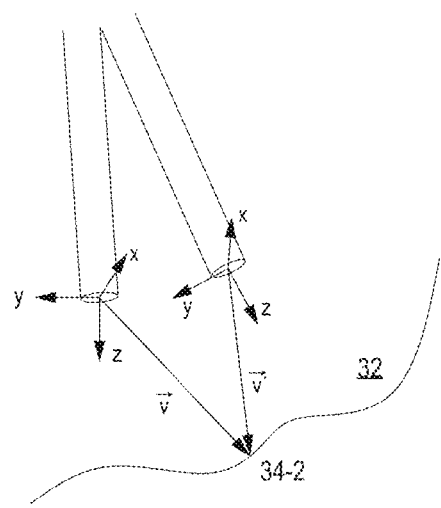
FIG. 8 is a representation of how the image sensor captures the same real point in different positions of its viewing field.

FIG. 8 illustrates how the same real point 34-2 is captured by one image sensor 16 in different positions from different positions. The xyz reference system remains constant, also the reference plane 48, which is the xy plane here. In the first spatial position, to the left, appears the real point 34-2 with the coordinates of a vector $\vec{v}$. In the second spatial position, to the right, appears the real point 34-2 with the coordinates of a vector $\vec{v}'$. The same real point 34-2 thus appears from the view of the image sensor 14 in conjunction with the depth information at two different coordinates. By determining enough point pairs of image points 34-1, which each image the same real point 34-2, the position change of the viewing field 46 of the image sensor 16 can be determined.

Figure 9:
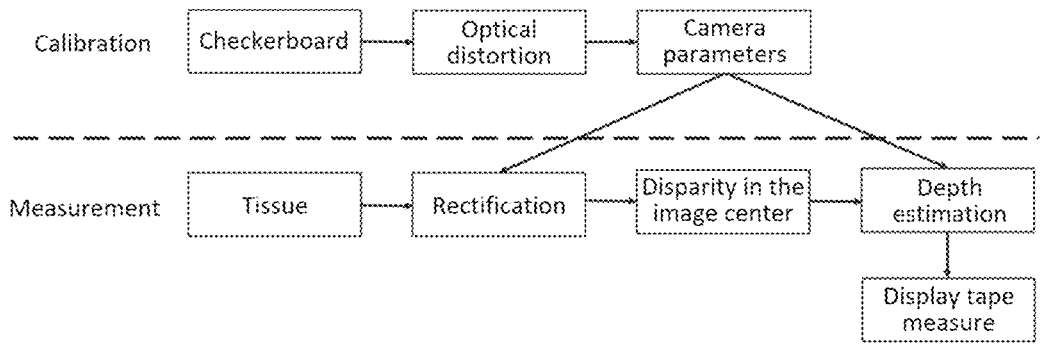
FIG. 9 is a schematic representation of the steps to be carried out to display a distance on a display device according to one embodiment.

FIG. 9 shows, in the case of a preferred embodiment, a schematic representation of the steps to be carried out to display a distance as measurement information 30 in the form of a tape measure on a display device 28. First, the image sensor 16, which is for example part of a video camera of a video endoscope, is calibrated. A possible optical distortion in the recorded images of the image sensor 16 is identified via the representation of checkerboards. The camera parameters are then determined in the subsequent calibration process.

The measurement starts with the recording of images of the tissue or of the anatomical structure 22. The camera parameters determined during the calibration process can be used for subsequent rectification, in which geometric distortions in the image data can be eliminated, which arise for example due to incorrect orientation of the camera. Then, based on the disparity in the image center of the recorded images, the depth is estimated. If the corresponding depth information is known, the distance can then be determined and a corresponding tape measure displayed in the image.

Figure 10:
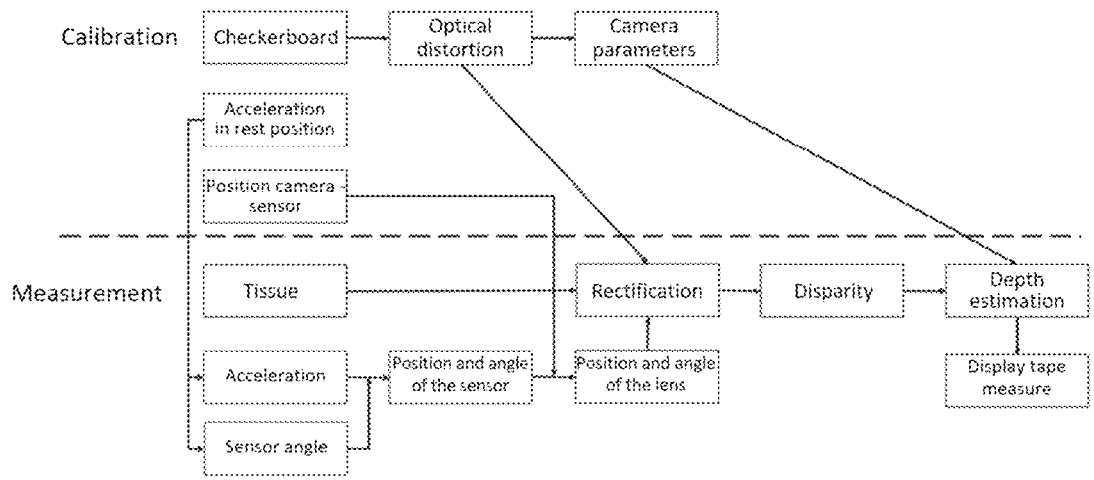
FIG. 10 is a schematic representation of the depth reconstruction based on an optical sensor and an additional movement sensor according to one embodiment.

FIG. 10 shows a schematic representation of the depth reconstruction based on the camera and an additional movement sensor. The movement sensor is for example an acceleration sensor, which can be integrated in the camera. The acceleration sensor registers the movements of the camera and by double integration of the acceleration, a quantitative value is obtained for the movement of the camera.

Unlike FIG. 9, further method steps are shown in FIG. 10. Thus, information regarding the position and angle of the optical lens of the camera is identified via the acceleration of the movement sensor in rest position (by gravity) and the acceleration and the sensor angle (with respect to the gravitational axis) of the acceleration sensor during the movement. This information can then be used for a more precise rectification.

Figure 11:
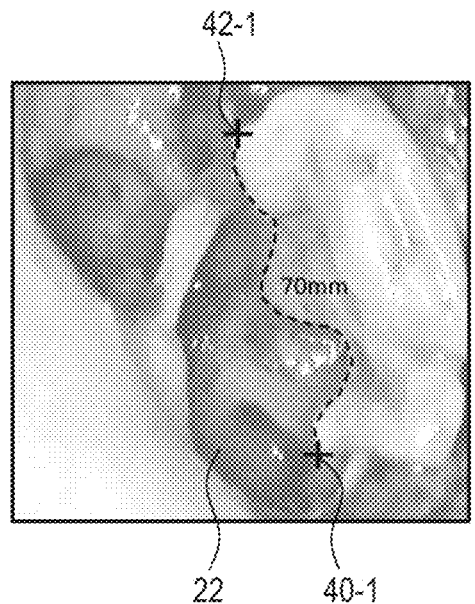
FIGS. 11 and 12 are further image recordings of an anatomical structure.
Figure 12:
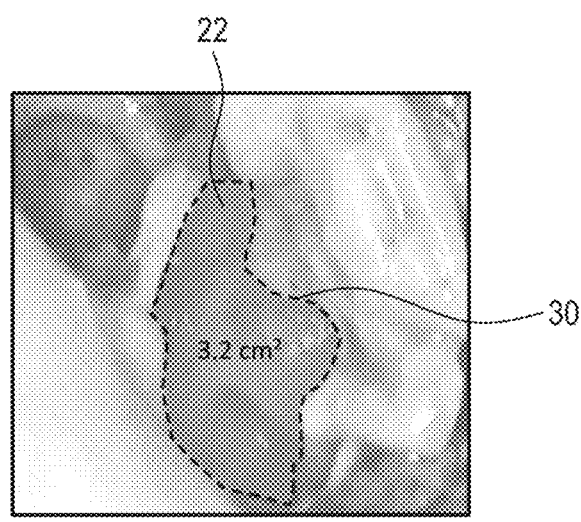

FIGS. 11 and 12 shows further image recordings of an anatomical structure 22 and a contour determination along the border of the anatomical structure 22. This is in particular possible when the translation and rotation of the viewing field of the image sensor 16 is known. This can, as shown for example in FIG. 10, take place by measuring using an acceleration sensor, which is mechanically coupled to the image sensor 16.

Therefore, not only can measurement result information 30 in the form of a distance, i.e. the shortest segment between the two coordinate points, be calculated between the image start point 40-1 and the image end point 42-1, but measurement result information 30 in the form of a curvilinear contour can also be calculated.

Through the identified translation of the image sensor 16 between the recording of different images of a video sequence, it is possible to track the path along which the image sensor 16 has moved during the medical examination. This can for example take place on the basis of a plurality of image or real sequential points 44-1, 44-2.

It is shown in FIG. 11 that a curvilinear boundary of an anatomical structure 22 can for example be measured as a result. It is shown in FIG. 12 that it is even possible to measure the area content or the circumference of the anatomical structure 22.

Overall, a simple and versatile measuring function for size determination of an anatomical structure is therefore provided by the measuring method presented and the corresponding measuring system.

It is understood that the embodiments shown are only to be understood as an example and that further variations are possible without departing from the concept of the present disclosure. The embodiments shown should therefore not be understood as limiting the scope of protection.

The invention claimed is:

1. A measuring method comprising:
  recording a first image of a scene, wherein recording takes place using an image sensor, in front of which an optical system is arranged, wherein, in the first image, a first plurality of first image points image a corresponding first plurality of first real points of the scene by means of the image sensor and wherein an image start point of the first plurality of first image points defines a real start point in the scene, wherein, when the first image is recorded, a viewing field of the image sensor is located in a first spatial position relative to the scene;
  identifying first depth information which describes, at least for a first subset of the first plurality of first image points, including the image start point, a respective distance of a first real point of the first plurality of first real points imaged by a first image point from a reference plane;
  recording a second image of the scene, wherein recording takes place using the image sensor, wherein, in the second image, a second plurality of second image points image a corresponding second plurality of second real points of the scene by means of the image sensor and wherein an image end point of the second plurality of second image points defines a real end point in the scene, wherein, when the second image is recorded, the viewing field of the image sensor is located in a second spatial position relative to the scene, which differs from the first spatial position;

identifying second depth information which describes, at least for a second subset of the second plurality of second image points, including the image end point, a respective distance of a second real point of the second plurality of second real points imaged by a second image point from the reference plane;

determining a group of point pairs, which each contain a first image point from the first plurality of first image points and a second image point from the second plurality of second image points, which correspond to one another in such manner that the first and the second image point of a point pair image the same real point;

determining a spatial position change of the viewing field of the image sensor on the basis of the group of point pairs;

calculating measurement result information based on a first position of the image start point on the image sensor, a second position of the image end point on the image sensor, depth information for the image start point and/or the image end point, the imaging properties of the optical system and the spatial position change of the viewing field, wherein the measurement result information is a length or an area in the scene; and outputting the measurement result information.

2. The measuring method according to claim 1, further comprising:

recording a third image of the scene, wherein recording takes place using the image sensor, in the third image, a third plurality of third image points image a corresponding third plurality of third real points of the scene by means of the image sensor and an image sequential point of the third plurality of third image points defines a real sequential point in the scene, wherein, when the third image is recorded, the viewing field of the image sensor is located in a third spatial position relative to the scene, which differs from the first and the second spatial position;

identifying third depth information which describes, at least for a third subset of the third plurality of third image points, including the image sequential point, a respective distance of a third real point of the third plurality of third real points imaged by a third image point from the reference plane;

determining a further group of point pairs, which each contain a second image point from the second plurality of second image points and a third image point from the third plurality of third image points, which correspond to one another in such manner that the second and the third image point of a point pair image the same real point;

determining a further spatial position change of the viewing field of the image sensor on the basis of the further group of point pairs;

wherein calculating the measurement result information is also based on a third position of the image sequential point on the image sensor and the further spatial position change of the viewing field or further measurement result information is calculated based on a third position of the image sequential point on the image sensor and the further spatial position change of the viewing field.

3. The measuring method according to claim 1, wherein after recording the first image and before recording the second or the third image, further comprising:

recording at least one intermediate image such that a sequence is formed beginning with the first image, continued over the at least one intermediate image and ending with the second or the third image, wherein, in each intermediate image, a further plurality of further image points image a corresponding further plurality of further real points of the scene by means of the image sensor and wherein, when the intermediate image is recoded, the viewing field of the image sensor is located in a further spatial position relative to the scene, which differs from the previous spatial position within the sequence;

after recording an intermediate image of the at least one intermediate image:

identifying further depth information, which describes, at least for a further subset of the further plurality of further image points, a respective distance of a further real point of the further plurality of further real points imaged by a further image point from the reference plane;

determining an intermediate group of point pairs, which each contain a first sequence image point from the further plurality of further image points in the intermediate image and a second sequence image point in a previous image from the sequence, which correspond to one another in such manner that the first and the second sequence image point of a point pair image the same real point;

wherein determining the spatial position change or the further spatial position change also takes place on the basis of the at least one further intermediate group of point pairs.

4. The measuring method according to claim 1, wherein at least one part of the first and second depth information is obtained from stereo image information.

5. The measuring method according to claim 1, wherein the measurement result information includes a distance between the real start point and the real end point.

6. The measuring method according to claim 1, wherein the measurement result information includes the length of a segment along a contour between the real start point and the real end point.

7. The measuring method according to claim 1, wherein the measurement result information includes the content of an area, whose boundary is identified taking into account the real start point and the real end point.

8. The measuring method according to claim 1, wherein at least one part of the first and second depth information is obtained from time-of-flight information provided by the image sensor or a depth image sensor.

9. The measuring method according to claim 1, wherein at least one part of the first and second depth information is obtained from focus information of the optical system.

10. The measuring method according to claim 1, wherein recording the first and/or the second image takes place by a manual user action.

11. The measuring method according to claim 1, wherein the spatial position change of the viewing field of the image sensor is determined taking into account movement data, which is recorded by a movement sensor arranged stationary relative to the image sensor.

12. The measuring method according to claim 1, wherein calculating the measurement result information includes a first calculation of first coordinates of the real start point in a unit of length and a second calculation of second coordinates of the real end point in the unit of length and wherein the measurement result information is calculated on the basis of the first and second coordinates.

13. The measuring method according to claim 1, wherein at least one region of the scene captured by the image sensor is illuminated at least temporarily with a pattern.

14. A measuring device comprising:
an image sensor, in front of which an optical system is arranged; and
a processor configured to:
record a first image of a scene, wherein recording takes place using an image sensor, in front of which an optical system is arranged, wherein, in the first image, a first plurality of first image points image a corresponding first plurality of first real points of the scene by means of the image sensor and wherein an image start point of the first plurality of first image points defines a real start point in the scene, wherein, when the first image is recorded, a viewing field of the image sensor is located in a first spatial position relative to the scene;
identify first depth information which describes, at least for a first subset of the first plurality of first image points, including the image start point, a respective distance of a first real point of the first plurality of first real points imaged by a first image point from a reference plane;
record a second image of the scene, wherein recording takes place using the image sensor, wherein, in the second image, a second plurality of second image points image a corresponding second plurality of second real points of the scene by means of the image sensor and wherein an image end point of the second plurality of second image points defines a real end point in the scene, wherein, when the second image is recorded, the viewing field of the image sensor is located in a second spatial position relative to the scene, which differs from the first spatial position;
identify second depth information which describes, at least for a second subset of the second plurality of second image points, including the image end point, a respective distance of a second real point of the second plurality of second real points imaged by a second image point from the reference plane;
determine a group of point pairs, which each contain a first image point from the first plurality of first image points and a second image point from the second plurality of second image points, which correspond to one another in such manner that the first and the second image point of a point pair image the same real point;
determine a spatial position change of the viewing field of the image sensor on the basis of the group of point pairs;
calculate measurement result information based on a first position of the image start point on the image sensor, a second position of the image end point on the image sensor, depth information for the image start point and/or the image end point, the imaging properties of the optical system and the spatial position change of the viewing field, wherein the measurement result information is a length or an area in the scene; and
output the measurement result information.

15. The measuring device according to claim 14, further comprising a light source that illuminates at least one region of the scene captured by the image sensor at least temporarily with a pattern.

* * * * *